United States Patent [19]

Shigesada et al.

[11] 4,411,999
[45] Oct. 25, 1983

[54] IMMOBILIZATION OF ENZYMES ON GRANULAR GELATIN

[75] Inventors: Shigeki Shigesada; Hironoshin Kitagawa; Toshio Mihara; Yoshiaki Ishimatsu, all of Machida, Japan

[73] Assignee: Denki Kagaku Kogyo Kabushiki Kaisha, Tokyo, Japan

[21] Appl. No.: 306,870

[22] Filed: Sep. 29, 1981

[51] Int. Cl.³ .................... C12N 11/02; C12N 11/00
[52] U.S. Cl. .................................... 435/177; 435/174
[58] Field of Search ................ 435/174, 177, 180, 182

[56] References Cited

U.S. PATENT DOCUMENTS 3,838,007  9/1974  Van Velzon .................... 435/182 X
3,859,169  1/1975  O'Driscoll et al. ................ 435/182
4,163,691  8/1979  Deros et al. .................... 435/182 X
4,266,029  5/1981  Branner-Jorgenson ............ 435/176

Primary Examiner—David M. Naff
Attorney, Agent, or Firm—Oblon, Fisher, Spivak, McClelland & Maier

[57] ABSTRACT

A process for producing an immobilized enzyme composition comprises simultaneously reacting a non-proteolytic enzyme and a water soluble-multifunctional reagent with a non-hardened granular gelatin in an aqueous medium wherein the reacting is carried out in the presence of a water-soluble protein polymer compound in an amount of from 0.01 to 2 parts by weight relative to one part of the non-proteolytic enzyme. The non-proteolytic enzyme forms a uniform film on the surface of the granular gelatin and the bond between the non-proteolytic enzyme and the granular gelatin is strengthened by the water soluble protein polymer.

12 Claims, No Drawings

IMMOBILIZATION OF ENZYMES ON GRANULAR GELATIN

BACKGROUND OF THE INVENTION

1. Field of the Invention

The present invention relates to a process for producing an immobilized enzyme composition. Particularly, the present invention relates to a process for producing an immobilized enzyme composition which comprises simultaneously reacting a non-proteolytic enzyme and a water-soluble protein polymer compound with non-hardened granular gelatine by means of a water-soluble multi-functional compound.

2. Description of the Prior Art

There have hitherto been various proposals for the production of an immobilized granular enzyme wherein an enzyme is bonded to a water-insoluble granular carrier.

For instance, there is a method in which glucose isomerase is bonded to a granular ion exchange resin (Yokote et al., Die Starke 27, 302 (1975)), a method wherein glucoamylase is bonded to a porous ceramics carrier (D. D. Lee et al., Die Starke 27, 384 (1975)), or a method in which aminoacylase is bonded to e.g. acrylamide in such a manner that an aqueous solution containing an enzyme or an enzyme-containing bacteria and a water-soluble monomer is polymerized and granulated (T. Mori et al., Enzymologia 43 213 (1972)).

Further, there is a method for obtaining an immobilized granular enzyme, which comprises suspending an enzyme in an aqueous solution of gelatine, adding this suspension dropwise to an organic solvent which is immiscible or hardly miscible with water, thereby to form granules, and then treating them with a multi-functional reagent (U.S. Pat. No. 3,838,007 of Sept. 24, 1974, Japanese Patent Publication No. 18794/77), a method in which an enzyme-containing solution is absorbed in a high molecular weight porous hardened protein capable of absorbing water in an amount of from 2 to 8 times the dry weight of the polymer, and then a glutaraldehyde solution is added (DP 2,636,206 of Aug. 12, 1976, Japanese Laid-Open Patent Application No. 41489/78), a method which comprises treating gelatine-coated sand particles with glutaraldehyde, mixing them with a paste comprising an enzyme and polyethylene imine and then treating them with glutaraldehyde (U.S. Pat. No. 4,266,029), or a method in which a non-proteolytic enzyme and a water-soluble multifunctional reagent are reacted with granular gelatine in an aqueous medium (Japanese Laid-Open Patent Application No. 157892/79).

Among these conventional methods, the inventions disclosed in the Japanese Patent Publication No. 18794/77 (U.S. Pat. No. 3,838,007) and the Japanese Laid-Open Patent Application No. 41489/78 (DP 2,636,206) are comparable with the present invention. In the former, an enzyme is suspended in an aqueous gelatine solution and then granulated, and in the latter, an aqueous enzyme solution is absorbed in a water absorptive hardened protein. Thus, in each case, the enzyme is excessively distributed throughout the entire inner structure of the carrier granules and immobilized. Accordingly, if such an immobilized enzyme is used for an enzymatic reaction with a substrate, the substrate and the reaction product encounter undesirable diffusion resistance in the inner structure of the carrier granules, whereby the apparent enzymatic reaction rate is decreased, resulting in a decrease of the efficiency of the enzyme. On the other hand, the reaction product tends to be locally concentrated within each granule, and thus it is likely that undesirable side reactions are thereby led. Especially when a polymer substrate is used, the enzymatic reaction rate is considerably reduced as such a substrate has a small diffusion velocity into the carrier granules.

A conventional method which is closest to the present invention is the above-mentioned Japanese Laid-Open Patent Application No. 157892/79, in which an enzyme solution and a multi-functional cross linking agent are simultaneously added to and reacted with a non-hardened water-soluble gelatine. According to this method, the gelatine starts to swell from its surface, and at the same time, the cross linking reaction proceeds from the surface. Consequently, a dense net work structure is formed on its surface before the enzyme diffuses into the inside of the gelatine granules. Accordingly, the enzyme is hardly able to penetrate into the inside of the gelatine granules and it undergoes a cross linking reaction with the gelatine to form an insoluble enzyme locally concentrated at the gelatine surface. Thus, an immobilized enzyme composition having a high enzymatic efficiency is obtainable which is free from a decrease in the apparent reaction rate due to the diffusion resistance against the penetration of the substrate into the inside of the granules.

However, the immobilized enzyme composition obtained by this method has a drawback that when used for a long period of time, its enzymatic activity decreases. This is a serious problem when it is used as an industrial catalyst.

Namely, it has been found tha when the enzyme composition is used for a long period of time in an industrial reactor such as a fixed bed reactor, the enzyme locally concentrated at the surface of the gelatine granules splits from the gelatine granules by the breakage of the chemical bond between the enzyme and the gelatine, and the enzyme layer is thus peeled off, thereby resulting in a decrease of the enzymatic activity. This is caused by the fact that the bond between the enzyme and gelatine by means of the multi-functional cross linking agent is weak.

SUMMARY OF THE INVENTION

The present inventors have conducted an extensive research to eliminate this drawback, and, as a result, have succeeded in the production of an immobilized enzyme composition which can be effectively used for a long period of time even in an industrial fixed bed reactor and which has an extremely high enzymatic activity. Namely, it has been found that if a water-soluble protein polymer highly reactive with a multi-functional cross linking agent is used in the immobilization of a non-proteolytic enzyme, it is possible to considerably improve the stability and at the same time to prevent excessive penetration of the enzyme into the inside of the gelatine carrier at the time of immobilization, and thus it is possible to obtain an immobilized enzyme composition having a high activity. Further, it has been found that the bond of the three components, i.e. the protein the enzyme and the gelatine, is strong, and accordingly, the immobilized enzyme composition has a superior physical strength and is capable of being used in a fixed bed reactor of an industrial scale.

The present invention has been accomplished on the basis of the above findings. It is an object of the present invention to provide an immobilized enzyme composition having a high activity.

Generally, the present invention relates to a process for producing an immobilized enzyme composition having a high activity and good stability, in which a non-proteolytic enzyme is bonded together with a water-soluble polymer compound to a granular gelatine by a water-soluble multi-functional cross linking agent.

DETAILED DESCRIPTION OF THE PREFERRED EMBODIMENTS

Now, the invention will be described in detail.

In the present invention, the non-proteolytic enzyme is meant for an enzyme which is inactive for the hydrolytic decomposition of a protein. Such an enzyme may be selected from a wide range of known enzymes for the purpose of the present invention, and for example, there may be mentioned glucoamylase, $\alpha$-amylase, $\beta$-amylase, isoamylase, pullulanase, or invertase. These enzymes may be from any source or origin. These enzymes may be used in a form of a crude enzyme recovered from a culture medium or in a form of a refined enzyme obtained by a usual refining method.

The ratio of the granular gelatine to the enzyme may be widely varied depending upon the particular enzyme to be used. However, this ratio is usually within a range of from 100:1 to 2:1, preferably from 20:1 to 5:1, by weight.

If the ratio is less than 100:1, the amount of enzyme is not adequate, and the immobilized enzyme thereby obtained has a low activity. On the other hand, if the ratio exceeds 2:1, the amount of the enzyme is too much, and there will be an enzyme left which can not effectively bonded to the surface of the granular gelatine, thus resulting in a loss of the enzyme.

As the water-soluble protein polymer compound which may be used in the present invention, for example, albumin, gelatine, casein or soybean protein, may be mentioned. They may be used alone or in combination.

The ratio of the enzyme to the water-soluble protein polymer compound may be varied depending upon the kind and purity of the enzyme and the particular combination with the water-soluble polymer compound. However, the ratio is usually within a range of from 1:0.01 to 1:2, preferably from 1:0.02 to 1:1, by weight. If the ratio is less than 1:0.01, the amount of the water-soluble protein polymer compound is too small to be effective, and if the ratio is more than 1:2, the number of bonding points on the granular gelatine for the enzyme becomes to be too small and undesirable elution of the enzyme is likely to occur during the enzymatic reaction.

The water-soluble multi-functional cross linking agent which may be used in the present invention, contains, in its molecule, 2 or more functional groups which are reactive with the amino acid residue of a protein. Specific examples of the water-soluble multi-functional cross linking agent which may be preferably used in the present invention, are dialdehydes represented by the general formula $OHC-(CH_2)_x-CHO$ (where x represents an integer of from 0 to 5), for example glutaraldehyde, or polyaldehydes such as dialdehyde starch.

The ratio of the enzyme to the water-soluble multi-functional reagent may be varied within a wide range. However, it is preferred that the ratio of the enzyme to the water-soluble multi-functional cross linking agent is within a range of from 1:0.01 to 1:2, more preferably from 1:0.05 to 1:1, by weight. If the ratio is less than 1:0.01, the bonding of the enzyme to the granular gelatine or the cross linking of the granular gelatine will be inadequate, thus leading to undesirable elution of the enzyme and the gelatine during the enzymatic reaction, and the strength tends to be inadequate. On the other hand, if the ratio exceeds 1:2, the number of bonding points on the granular gelatine for the enzyme becomes to be excessive, thus leading to an undesirable decrease of the enzyme activity.

The granular gelatine in the present invention is a water-soluble gelatine obtainable by treating a skin or bone of an animal with hot water and refining and drying the extracted product thereby obtained, and it may be in a form of flakes as pulverized, spherical granules or pellets, and not in a form of fine powder. Among these shapes, flakes as pulverized are preferred. Further, they may be formed into spherical granules or pellets, as the case requires.

The size of the granular gelatine is usually within a range of from 0.1 to 2 mm, preferably from 0.2 to 1 mm. If the size exceeds 2 mm, the effective surface area decreases and the activity decreases accordingly. On the other hand, if the size is less than 0.1 mm, when it is used in a fixed bed reactor, a pressure loss becomes undesirably great.

The preparation of the immobilized enzyme composition according to the present invention is carried out in the following order.

(1) The non-proteolytic enzyme and the water-soluble protein polymer compound are dissolved in water.
(2) To the aqueous solution thereby obtained, the water-soluble multi-functional reagent is added and mixed.
(3) The water-soluble granular gelatine and the aqueous mixed solution obtained by step (2) are mixed and stirred, and they are reacted at 5° to 4° C. for from 5 to 60 minutes.
(4) After the completion of the reaction, the product is adequately washed with water, and, if necessary, dried.

When the granular gelatine is to be reacted with the enzyme and the water-soluble protein polymer compound by means of the water-soluble multi-functional reagent, the granular gelatine is mixed and stirred with an aqueous solution (hereinafter referred to simply as an "aqueous mixed solution") prepared by adding and mixing the water-soluble multi-functional reagent with a mixed solution comprising the enzyme and the water-soluble protein polymer compound dissolved in an aqueous medium having a pH of from 4 to 9, preferably from 5 to 7. In this case, the ratio of the granular gelatine and the aqueous mixed solution is within a range of from 1:0.2 to 1:3, preferably from 1:0.5 to 1:2.5, by weight. If the ratio is less than 1:0.2, the amount of water relative to the granular gelatine is inadequate and it is impossible to have the enzyme bonded uniformly to the surface of the gelatine granules. On the other hand, if the ratio exceeds 1:3, the amount of water relative to the gelatine is excessive, and the gelatine tends to swell too much by absorption of water, thus leading to a decrease of the strength of the immobilized enzyme granules.

The mixing and stirring of the granular gelatine and the aqueous mixed solution can be carried out manually or mechanically, and the time for the stirring may be varied depending upon the amounts of the components and the temperature, but it is usually sufficient to continue the stirring for from 5 to 60 minutes to obtain a granular immobilized composition of good quality.

The temperature for the immobilization treatment according to the present invention, may be varied within a range in which the stability of the enzyme used is not deteriorated, and it is usually within a range of from 5° to 40° C., preferably from 10° to 30° C.

In the present invention, upon completion of the bonding, the composition is treated by a usual method, for instance, by adequate washing with water and drying, or it may be stored in a wet condition unil it is used.

In the immobilized enzyme composition of the present invention, the non-proteolytic enzyme forms a uniform film on the surface of the granular gelatine, and the chemical bond between the non-proteolytic enzyme and the granular gelatine is strengthened by means of the water-soluble protein polymer compound having a high reactivity with the water-soluble multi-functional reagent. Accordingly, the immobilized composition is highly active and stable, and it has a great mechanical strength adequately qualified to be used in a fixed bed reactor.

The immobilized enzyme composition of the present invention is safe to the human body, and may be used in the field of the food processing.

As described hereinabove, according to the present invention, an immobilized enzyme composition which is highly active and stable and which is quite useful for an industrial application, can be presented in an extremely simple manner.

Now, the present invention will be described with reference to the Examples. However, it should be understood that the invention is not limited by these Examples.

EXAMPLE 1

Dissolved in 15 ml. of an aqueous glucoamylase solution (prepared by Nagase Sangyo K.K. from Aspergillus niger, and containing 4 g. of the enzyme having an activity of 30,000 u/g refined with isopropanol) was 0.5 g. of egg albumin. To the aqueous solution thereby obtained, 4 ml. of glutaraldehyde (prepared by Nagase Sangyo K.K., a 50 w/w % aqueous solution) was mixed, and then 20 g. of dried gelatine flakes having a water content of not more than 16% and mostly having a grain size of from 0.3 to 0.8 mm (prepared by Nitta Gelatine K.K.) were added. The mixture was stirred for 10 minutes in a mortar. After leaving the mixture to stand still for 30 minutes, 400 ml. of water was added to the obtained granular immobilized product for washing and then filtered.

This washing operation was repeated 5 times, and then the product was dried at 40° C. for 10 hours by blowing air thereto. The obtained immobilized product (23.0 g.) exhibited and specific activity of 1160 u/g.

One unit (u) of the activity used here, is meant for the amount of the enzyme capable of forming $100\gamma$ of glucose per minute at 40° C. using, as the substrate, a solution of 20% dextrin (prepared by Nichiden Kagaku K.K., Amucol No. 1, D.E. 16.0) in 0.05 M acetic acid buffer (pH 4.5).

EXAMPLE 2

While stirring an aqueous solution containing 10% of skim milk, a 5% acetic acid aqueous solution was gradually added thereto to adjust the pH to 4.5 and to precipitate casein, and then the casein-precipitated slurry was filtered under suction by means of Nutsche, whereby a wet casein was obtained. The obtained wet casein was dispersed in water to bring the solid concentration to be 10% (w/v), and while stirring the dispersion, 2 N NaOH was gradually added to adjust the pH to 7, whereby an aqueous solution having the casein dissolved therein was obtained. Five ml. of the 10 w/v % casein aqueous solution was added to 10 ml. of an aqueous glucoamylase solution (prepared by Nagase Sangyo K.K. from Rhizopus delemer, an aqueous solution containing 30% of the enzyme having an activity of 40,000 u/g). To the aqueous mixed solution thereby obtained 4 ml of glutaraldehyde (prepared by Nagase Sangyo K.K., a 50 w/w % aqueous solution) was mixed, and then 20 g. of dried gelatine flakes having a water content of not more than 16% and mostly having a grain size of from 0.3 to 0.8 mm (prepared by Nitta Gelatine K.K.) were added, and stirred at room temperature for 10 minutes in a mortar. After leaving the mixture to stand still for 20 minutes, the immobilized product thereby obtained was washed with water (5 times each with 400 ml. of water) and then filtered and dried at 40° C. for 10 hours by blowing air thereto. The granular immobilized product (21.8 g.) thereby obtained, exhibited an activity of 970 u/g.

EXAMPLE 3

Dissolved in 4 ml. of an aqueous $\beta$-amylase solution (prepared by Tokyo Kasei K.K., and containing 1 g. of the enzyme having an activity of 3,400 u/g) was 0.3 g. of egg albumin. To the aqueous solution thereby obtained, 0.7 ml. of glutaraldehyde (a 50 w/w % aqueous solution) was mixed, and then 5 g. of dried gelatine flakes having a water content of not more than 16% and mostly having a grain size of from 0.3 to 0.8 (prepared by Nitta Gelatine K.K.) was added and stirred at room temperature for 10 minutes. After leaving the mixture to stand still for 20 minutes, the immobilized product thereby obtained was washed with water (5 times each with 200 ml. of water), and then filtered and dried at 40° C. for 5 hours by blowing air thereto. The immobilized product thereby obtained weighed 5.6 g. and had an activity of 52 u/g.

One unit (u) of the activity used here is meant for the amount of the enzyme capable of forming a reducing sugar corresponding 10 mg. of glucose per minute at 40° C. using, as the substrate, 0.56% soluble starch in 0.05 M acetic acid buffer (pH 4.5).

EXAMPLE 4

Dissolved in 4 ml. of an aqueous pullulanase solution (i.e. a solution prepared by dissolving pullulanase (prepared by Nagase Seikagaku K.K.) in water and having an activity of 850 units/ml., where the activity unit is defined such that one unit (u) is meant for the amount of the enzyme capable of forming 100 $\mu$g of a reducing sugar per minute from pullulan at 40° C. at pH 5.5 was 0.2 g. of egg albumin. To the aqueous solution thereby obtained, 2 ml. of glutaraldehyde (prepared by Nagase Sangyo K.K., a 50 w/w aqueous solution) was added, and then 10 g. of the granular gelatine similar to the one used in Example 1 was added, and stirred at room temperature for 10 minutes in a mortar. After leaving the mixture to stand still for 40 minutes at room temperature, the immobilized product thereby obtained was added to 200 ml. of water and stirred for 60 minutes. The immobilized pullulanase obtained after the washing with water and the filtration, had an activity of 800 u/g as a dry product.

COMPARATIVE EXAMPLE 1

(Example in which no water-soluble polymer compound was not used)

Added to 20 g. of dried gelatine flakes having a water content of not more than 16% and mostly having a granule size of from 0.3 to 0.8 mm (prepared by Nitta Gelatine K.K.) was an aqueous mixed solution comprising 15 ml. of an aqueous glucoamylase solution (prepared by Nagase Sangyo K.K. from Aspergillus niger, and containing 4 g. of the enzyme refined by isopropanol and having an activity of 30,000 u/g) and 4 ml. of glutaraldehyde (prepared by Nagase Sangyo K.K., a 50 w/w % aqueous solution). The mixture was stirred at room temperature for 10 minutes in a mortar. After leaving the mixture to stand still for 30 minutes, the granular immobilized product thereby obtained was washed with 400 ml. of water and then filtered and dried at 40° C. for 10 hours by blowing air thereto. The granular immobilized product thereby obtained exhibited an activity of 1350 u/g.

APPLICATION EXAMPLE 1

The changes of the activities with time were measured by maintaining the granular immobilized glucoamylase products obtained by Example 1 and Comparative Example 1, respectively, in an aqueous solution (pH 4.5) containing 25% of dextrin (prepared Nichiden Kagaku K.K., Amycol No. 1, DE 16.0) at 50° C. The results thereby obtained are shown in the following Table.

TABLE

| Number of days | 0 | 20 | 40 | 60 | 80 |
| --- | --- | --- | --- | --- | --- |
| Example 1 | 1160 u/g | 1100 u/g | 950 u/g | 850 u/g | 700 u/g |
| Comparative Example | 1350 u/g | 950 u/g | 670 u/g | 450 u/g | 270 u/g |

From the above Table, it is apparent that the immobilized enzyme composition of the present invention has a long lasting high activity and has a superior stability.

COMPARATIVE EXAMPLE 2

(Example in which no water-soluble polymer compound was not used)

Added to 10 g. of dried gelatine flakes having a water content of not more than 16% and mostly having a granular size of from 0.3 to 0.8 mm (prepared by Nitta Gelatine K.K.) was an aqueous mixed solution comprising 15 ml. of an aqueous glucoamylase solution (prepared by Nagase Sangyo K.K. from Rhizopus delemer, an aqueous solution containing 20% of the enzyme having an activity of 40,000 u/g) and 4 ml. of glutaraldehyde (a 50 w/w aqueous solution). The mixture was stirred at room temperature for 10 minutes in a mortar. After leaving the mixture to stand still for 30 minutes, the granular immobilized product thereby obtained was washed with water (5 times each with 400 ml. of water). After filtration, the product was dried at 40° C. for 10 hours by blowing air thereto. The granular immobilized product thereby obtained, exhibited an activity of 680 u/g.

APPLICATION EXAMPLE 2

The changes of the activities with time were measured by maintaining the granular immobilized glucoamylase products obtained by the Example 2 and Comparative Example 2, respectively, in an aqueous solution (pH 4.5) containing 25% of dextrin (prepared by Nichiden Kagaku K.K., Amycol No. 1, DE 16.0) at 50° C. The results thereby obtained are shown in the following Table.

TABLE

| Number of days | 0 | 3 | 5 | 10 | 15 |
| --- | --- | --- | --- | --- | --- |
| Example 2 | 970 u/g | 950 u/g | 890 u/g | 820 u/g | 780 u/g |
| Comparative Example | 680 u/g | 545 u/g | 490 u/g | 320 u/g | 240 u/g |

From the above Table, it is apparent that the immobilized enzyme composition of the present invention has a long lasting high activity and has a superior stability.

COMPARATIVE EXAMPLE 3

(Example of Japanese Patent Publication No. 18794/77, U.S. Pat. No. 3,838,007)

Two grams of glucoamylase (prepared Nagase Sangyo K.K., and having an activity of 30,000 u/g as a dried product) was mixed with 100 ml. of an aqueous solution containing 10% by weight of gelatine, and was dissolved at 45° C., and the pH was adjusted to 7.0.

The enzyme-gelatine mixed solution thus obtained was dropwise added to 500 ml. of butylacetate while stirring and maintaining it at a temperature of 50° C. The obtained mixture was cooled to 10° C., and 5 ml. of an aqueous solution containing 25% by weight of glutaraldehyde was added and stirred for 20 minutes. Then, 1 l of ethanol was added, and the granules were dehydrated. Thereafter, the granules were divided into 4 portions, to which 200 ml. of aqueous glutaraldehyde solutions having various concentrations were respectively added, stirred for 30 minutes and then filtered, washed each with 1 l of water and freeze-dried. The immobilized products thereby obtained were such that glucoamylase was uniformly distributed within the granules. The activities and the strength thereof are shown in the following Table.

TABLE

| | Concentration of glutaraldehyde | Activities | Strength* |
| --- | --- | --- | --- |
| 1 | 0% | 625 u/g | 10 g/granule |
| 2 | 0.2% | 460 u/g | 25 g/granule |
| 3 | 0.5% | 250 u/g | 65 g/granule |
| 4 | 1.0% | 150 u/g | 85 g/granule |
| Immobilized product of Example 1 | | 1160 u/g | 165 g/granule |

Note:
*The strength was measured by Rheometer (made by Fudo Kogyo K.K. on the basis of the destruction strength of the granules swelled with water for 20 hours.

In the case where the glutaraldehyde concentration was high, the activity was high but the strength was too low to be packed in a column. When the glutaraldehyde concentration was increased, the strength was increased but the activity was considerable decreased.

COMPARATIVE EXAMPLE 4

(Example of Japanese Laid-Open Patent Application No. 41489/78, DP 2636206)

To 100 g. of gelatine similar to the one used in Example 1, 600 ml. of water was added, and the gelatine was dissolved at 60° C. Then, 15 ml. of an aqueous 36% formaline solution was added thereto and stirred. Upon expiration of 2 minutes, the mixture turned into a soft gel, which was coarsely crushed and dried at 115° C. for 15 hours. After pulverization, granules having a size of from 0.3 to 0.8 mm were collected by sieving. Ten grams of this hardened gelatine was mixed into 28 ml. of an aqueous glucoamylase solution similar to the one used in Example 1 to absorb the latter, and then a mixed solution comprising 2 ml. of an aqueous solution containing 25% of glutardialdehyde and 40 ml. of acetone, was added and reacted for cross linking at 30° C. for 60° C. while gently stirring the mixture. The thus formulated product was subjected to an after treatment in a manner similar to Example 1. The immobilized product thereby obtained, exhibited an activity of 2500 u/g as a dry product.

Ten grams of this immobilized product was subjected to the stabilization test in a manner similar to Application Example 1, whereby it was found that the activity (u/g as a dry product) was 1200 on the first day, 800 on the second day and 400 on the fifth day, and the product underwent deformation on the tenth day and it was impossible to measure the activity. Thus, it was found that the stability was extremely inferior.

We claim:

1. A process for producing an immobilized enzyme composition, which comprises:

simultaneously reacting a non-proteolytic enzyme, a water soluble multi-functional reagent and a water soluble protein polymer selected from the group consisting of casein, albumin, gelatin and soybean protein with a non-hardened granular gelatin in the form of flakes, spherical granules or pellets having a particle size within the range of from 0.1 to 2.0 mm to form a film of the non-proteolytic enzyme immobilized on the surface of said granular gelatine, said non-proteolytic enzyme, water soluble multi-functional reagent and water soluble protein polymer being in solution when reacted with said granular gelatin, and the weight ratio of the non-proteolytic enzyme to granular gelatin ranging from 1:2 to 1:100, the weight ratio of the non-proteolytic enzyme to water soluble multi-functional reagent ranging from 1:0.01 to 1:2, the weight ratio of the non-proteolytic enzyme to water soluble protein polymer ranging from 1:0.01 to 1:2 and the weight ratio of the granular gelatin to the aqueous medium ranging from 1:0.2 to 1:3.

2. The process of claim 1, wherein the water soluble multi-functional reagent is a dialdehyde of the formula: $OHC-(CH_2)_x-CHO$, wherein X is 0 or an integer from 1 to 5.

3. The process of claim 1, wherein the temperature of the immobilization reaction is within the range of from 5° to 40° C.

4. The process of claim 1, wherein the weight ratio of the non-proteolytic enzyme to the granular gelatine ranges from 1:5 to 1:20.

5. The process of claim 1, wherein the weight ratio of the non-proteolytic enzyme to the water soluble multi-functional reagent ranges from 1:0.05 to 1:1.

6. The process of claim 1, wherein the weight ratio of the non-proteolytic enzyme to the water-soluble protein polymer ranges from 1:0.02 to 1:1.

7. The process of claim 1, wherein the weight ratio of the granular gelatine to the aqueous medium ranges from 1:0.5 to 1:2.5.

8. The process of claim 1, wherein the non-proteolytic enzyme is glucoamylase, $\alpha$-amylase, $\beta$-amylase, isoamylase, pullulanase or invertase.

9. The process of claim 8, wherein said enzyme is glucoamylase.

10. The process of claim 2, wherein said dialdehyde is glutaraldehyde.

11. The process of claim 3, wherein said reaction temperature ranges from 10° to 30° C.

12. The process of claim 1, wherein the pH of the aqueous medium during the reaction ranges from 4 to 9.

* * * * *